United States Patent
Goldfain

(10) Patent No.: US 9,001,326 B2
(45) Date of Patent: Apr. 7, 2015

(54) METHOD AND APPARATUS FOR OBSERVING SUBSURFACES OF A TARGET MATERIAL

(75) Inventor: Ervin Goldfain, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 293 days.

(21) Appl. No.: 13/324,400

(22) Filed: Dec. 13, 2011

(65) Prior Publication Data
US 2013/0148326 A1  Jun. 13, 2013

(51) Int. Cl.
*G01J 4/00* (2006.01)
*G01N 21/00* (2006.01)
*G01N 21/47* (2006.01)
*G01B 11/24* (2006.01)
*A61B 5/00* (2006.01)
*G01J 3/02* (2006.01)
*G01N 21/88* (2006.01)
*G01N 21/49* (2006.01)
*G01N 21/21* (2006.01)

(52) U.S. Cl.
CPC .......... *G01N 21/4795* (2013.01); *A61B 5/0075* (2013.01); *G01J 3/0224* (2013.01); *G01J 3/0272* (2013.01); *A61B 5/441* (2013.01); *G01N 2021/8848* (2013.01); *A61B 5/4887* (2013.01); *G01N 21/49* (2013.01); *A61B 5/489* (2013.01); *G01N 2021/4792* (2013.01); *G01N 2201/0221* (2013.01); *G01N 21/474* (2013.01); *G01N 21/21* (2013.01); *A61B 5/0077* (2013.01)

(58) Field of Classification Search
None
See application file for complete search history.

(56) References Cited

U.S. PATENT DOCUMENTS

| | | | |
|---|---|---|---|
| 5,709,459 A | 1/1998 | Gourgouliatos | |
| 5,847,394 A * | 12/1998 | Alfano et al. | 250/341.8 |
| 6,032,071 A | 2/2000 | Binder | |
| 6,081,612 A * | 6/2000 | Gutkowicz-Krusin et al. | 382/128 |
| 6,106,457 A | 8/2000 | Perkins | |
| 6,324,417 B1 | 11/2001 | Cotton | |
| 6,522,407 B2 * | 2/2003 | Everett et al. | 356/369 |
| 6,587,711 B1 * | 7/2003 | Alfano et al. | 600/476 |
| 6,993,167 B1 * | 1/2006 | Skladnev et al. | 382/128 |
| 7,006,223 B2 | 2/2006 | Mullani | |
| 7,024,037 B2 | 4/2006 | Zhang | |
| 7,289,211 B1 * | 10/2007 | Walsh et al. | 356/369 |
| 7,290,882 B2 | 11/2007 | Collins | |
| 7,309,335 B2 | 12/2007 | Altshuler | |

(Continued)

FOREIGN PATENT DOCUMENTS

| AU | 4961597 | 5/1998 |
|---|---|---|
| AU | 725766 | 6/1998 |

(Continued)

*Primary Examiner* — Gordon J Stock, Jr.
(74) *Attorney, Agent, or Firm* — Guntin & Gust, PLC; Ed Guntin

(57) ABSTRACT

A system that incorporates teachings of the present disclosure may include, for example, a method for generating from a light source a light signal operating in a region of the light spectrum, modifying the light signal with a first polarization device having a first polarization state to generate a polarized light signal directed to a target, modifying a substantially specular reflection and a substantially diffused reflection of the polarized light signal generated from the target with a second polarization device having a second polarization state to generate mixed polarized light signals having a mixed polarization state, and adjusting the mixed polarization state to modify an observable range of subsurfaces of the target. Other embodiments are disclosed.

30 Claims, 8 Drawing Sheets

(56) References Cited

U.S. PATENT DOCUMENTS

| | | |
|---|---|---|
| 7,627,363 B2 * | 12/2009 | Yaroslavsky et al. .......... 600/473 |
| 7,898,670 B2 | 3/2011 | Berg |
| 7,916,910 B2 | 3/2011 | Cotton |
| 7,986,401 B2 * | 7/2011 | Lechocinski et al. ......... 356/73.1 |
| 8,223,322 B2 * | 7/2012 | Breugnot et al. ............. 356/73.1 |
| 2002/0087085 A1 * | 7/2002 | Dauga ............................ 600/476 |
| 2005/0228264 A1 * | 10/2005 | Grichnik ....................... 600/411 |
| 2005/0264813 A1 * | 12/2005 | Giakos .......................... 356/369 |
| 2006/0109342 A1 * | 5/2006 | Bazin .............................. 348/61 |
| 2006/0239547 A1 | 10/2006 | Robinson et al. |
| 2006/0247514 A1 * | 11/2006 | Panasyuk et al. ............. 600/410 |
| 2007/0024946 A1 * | 2/2007 | Panasyuk et al. ............. 359/253 |
| 2008/0063998 A1 * | 3/2008 | Liang et al. ..................... 433/29 |
| 2008/0075340 A1 | 3/2008 | Cotton |
| 2008/0090198 A1 * | 4/2008 | Liang et al. ..................... 433/29 |
| 2008/0304081 A1 | 12/2008 | Debevec et al. |
| 2009/0226049 A1 | 9/2009 | Debevec et al. |
| 2009/0245603 A1 * | 10/2009 | Koruga et al. ................. 382/128 |
| 2010/0185064 A1 * | 7/2010 | Bandic et al. ................. 600/306 |
| 2011/0184260 A1 | 7/2011 | Robinson et al. |
| 2011/0211047 A1 * | 9/2011 | Chhibber et al. ............... 348/47 |
| 2012/0013722 A1 * | 1/2012 | Wong et al. ..................... 348/66 |
| 2012/0321759 A1 * | 12/2012 | Marinkovich et al. ........ 426/231 |
| 2013/0307950 A1 * | 11/2013 | Aharon ........................... 348/65 |

FOREIGN PATENT DOCUMENTS

| | | |
|---|---|---|
| AU | 5232100 | 12/2000 |
| AU | 2006220441 | 4/2007 |
| CA | 2272290 | 5/1998 |
| CA | 2560364 | 3/2007 |
| EP | 1006876 | 5/2002 |
| EP | 1768060 | 3/2007 |
| EP | 1185853 | 8/2007 |
| EP | 2393063 | 7/2011 |
| GB | 2334099 | 8/1999 |
| GB | 2429385 | 2/2007 |
| GB | 2439469 | 12/2007 |
| JP | 2001504020 | 3/2001 |
| JP | 2003501651 | 1/2003 |
| JP | 2007190364 | 8/2007 |
| WO | WO-9822023 | 5/1998 |
| WO | WO-0075637 | 12/2000 |
| WO | WO2010/097218 | 9/2010 |

* cited by examiner

METHOD AND APPARATUS FOR OBSERVING SUBSURFACES OF A TARGET MATERIAL

FIELD OF THE DISCLOSURE

The present disclosure relates generally to a method and apparatus for observing subsurfaces of a target material.

BACKGROUND

Optical signal acquisition and processing methods can be useful in medical as well as industrial applications. For example, light signals can be used in some instances to penetrate a range of subsurfaces of a target material. The scattered light reflected from the target material can be used to generate micrometer resolution of three or two-dimensional images that are descriptive of the subsurfaces of the target material. In medical applications, these images can assist a physician to diagnose abnormalities in biological materials. In industrial applications, such images can provide engineers or other specialists insight into the subsurfaces of non-biological materials.

BRIEF DESCRIPTION OF THE DRAWINGS

Reference will now be made to the accompanying drawings, which are not necessarily drawn to scale.

DETAILED DESCRIPTION

Figure 1:
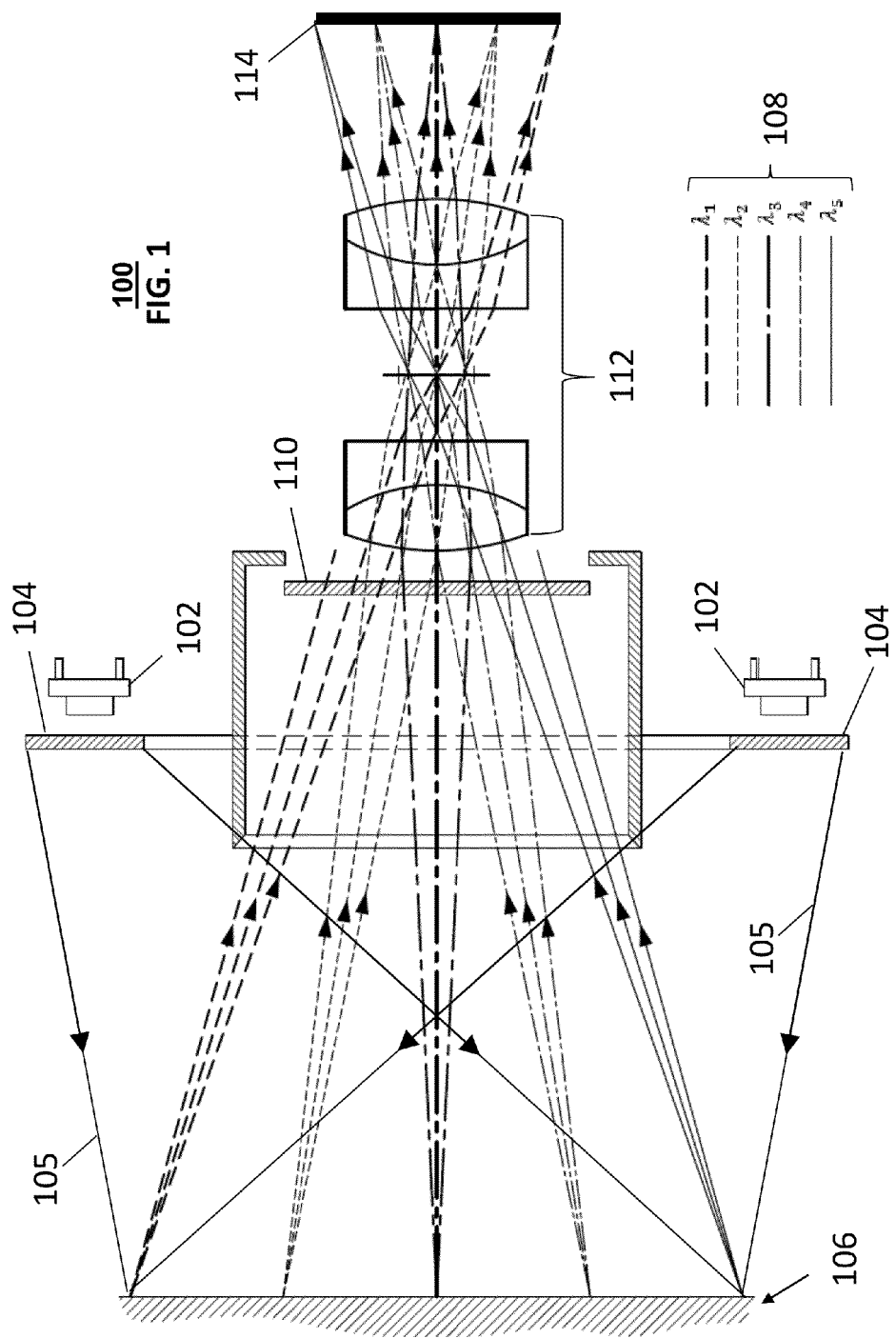
FIG. 1 depicts an illustrative embodiment of a device for observing subsurfaces of a target.

One embodiment of the present disclosure includes a device having a light source, first and second polarization elements, a mechanism, and an imager. The light source can be adapted to emit a light signal operating in a region of the light spectrum. The first polarization element can have a first portion that is incident with the light signal. The first portion can have a first polarization state for polarizing the light signal to generate a polarized light signal directed to a target tissue. The second polarization element can have a second portion that is incident with a substantially specular reflection of the polarized light signal emitted from a top surface of the target tissue and incident with a substantially diffused reflection of the polarized light signal emitted from subsurfaces of the target tissue. The second portion can have a second polarization state. A combination of the first polarization state and the second polarization state creates a mixed polarization state for generating mixed polarized light signals from the substantially specular reflection and the substantially diffused reflection of the polarized light signal. The mechanism can be adapted to adjust the mixed polarization state to modify the mixed polarized light signals, thereby adjusting an observable range of the subsurfaces of the target tissue. The imager can be adapted to present the adjusted observable range of the subsurfaces of the target tissue according to the modified mixed polarized light signals.

In one embodiment of the present disclosure, the imager can comprise an optical device and an image sensor. The optical device can comprise a plurality of optical devices. In another embodiment, the device can also comprise a second mechanism for controlling at least one of a zoom in feature of the plurality of optical devices, a zoom out feature of the plurality of optical devices, a focusing feature of the plurality of optical devices, or combinations thereof. In this embodiment, the second mechanism can comprise one or more subassemblies coupled to at least one of the plurality of optical devices for manually controlling at least one of the zoom in feature of the plurality of optical devices, the zoom out feature of the plurality of optical devices, the focusing feature of the plurality of optical devices, or combinations thereof. In one embodiment, at least a portion of the second mechanism can comprise a motor coupled to at least one of the plurality of optical devices for controlling at least one of the zoom in feature of the plurality of optical devices, the zoom out feature of the plurality of optical devices, the focusing feature of the plurality of optical devices, or combinations thereof.

One embodiment of the present disclosure includes a method for generating from a light source a light signal operating in a region of the light spectrum, modifying the light signal with a first polarization device having a first polarization state to generate a polarized light signal directed to a target, modifying a substantially specular reflection and a substantially diffused reflection of the polarized light signal generated from the target with a second polarization device having a second polarization state to generate mixed polarized light signals having a mixed polarization state, and adjusting the mixed polarization state to modify an observable range of subsurfaces of the target.

One embodiment of the present disclosure includes a method for assembling in a device a first polarization device and a light source for polarizing a light signal emittable by the light source according to a first polarization state of the first polarization device to generate a polarized light signal. The method further including assembling in the device a second polarization device for modifying a substantially specular reflection and a substantially diffused reflection of the polarized light signal generated by a target according to a second polarization state of the second polarization device. The method also including assembling in the device a mechanism for adjusting at least one of the first polarization state, the second polarization state, or both to modify an observable range of subsurfaces of the target.

One embodiment of the present disclosure includes a computer-readable storage medium having computer instructions, which when executed by a processor, configures the processor to cause a light source to emit a light signal at a desired range of wavelengths of light. The light signal can be polarized by a first polarizer having a first polarization state to generate a polarized light signal directed to a target. A substantially specular reflection and a substantially diffused reflection of the polarized light signal generated from the target can be modified with a second polarization device having a second polarization state to generate mixed polarized light signals having a mixed polarization state. The computer-readable storage medium can further have computer instructions, which when executed by a processor, configures the processor to cause a mechanism to adjust at least one of the first polarization state, the second polarization state, or both to modify an observable range of subsurfaces of the target.

Figure 2:
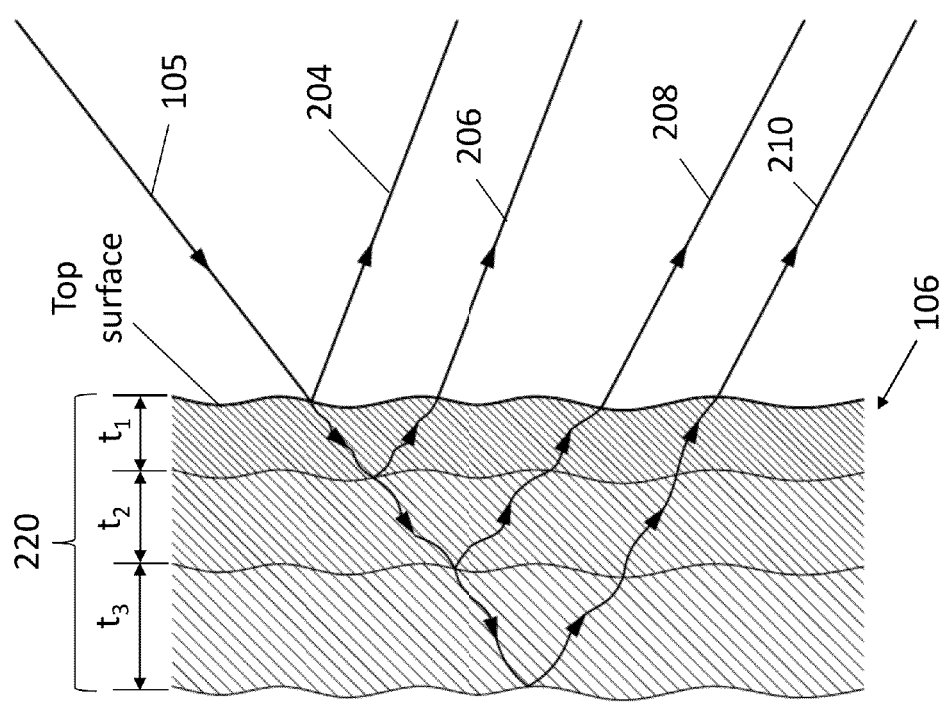
FIG. 2 depicts an illustrative embodiment of substantially specular and substantially diffused reflections of polarized light emitted from the target of FIG. 1.

FIGS. 1 and 2 depict an illustrative embodiment of a device 100 for observing a range of subsurface layers 220 of a target 106. The device 100 can comprise a light source 102 and a first polarizer 104 incident to light signals emitted by the light source 102. The light source 102 can comprise one or more tunable light sources such as tunable light emitting diodes (LEDs), or fibers coupled to one or more tunable broadband sources. Each tunable light source can be tuned to a range of one or more wavelengths of light 108 such as shown in FIG. 1, thereby enabling the user to control a color range of the light emitted by each tunable light source. The tunable light sources can be controlled in parallel so that each source transmits substantially the same light signals in unison, or individually so that each light source can be tuned to an independent range of wavelengths of light.

The light signals emitted by the light source 102 are polarized by a first portion of the first polarizer 104 that is incident with the light signal to generate a polarized signal 105 having a first polarization state, which is directed to a target 106. Different polarization techniques can be used for the first polarizer 104 such as, for example, linear polarization, circular polarization, elliptical polarization, and so on. For illustration purposes only, the first polarizer 104 is assumed to be a linear polarizer. The target 106 can consist of a biological material such as human tissue. Alternatively, the target 106 can consist of non-biological material such as fibers, or other compositions which may have subsurface features which can be penetrated by polarized light signals.

FIG. 2 depicts an illustrative embodiment of substantially specular and substantially diffused reflections of the polarized light 105 emitted from the target 106 of FIG. 1. In the illustration, the target 106 has subsurface layers 220. Each layer can be non-uniform and varying features. For example, the target 106 can be skin tissue, which includes different components such as blood vessels, fat, collagen fibers, and so on. Tissue components can characteristically reflect different wavelengths of light. For example, arteries tend to reflect red light, while veins reflect blue light. The differences in the color reflected from the target 106 can enable a user to analyze subsurface features of the target 106. In FIG. 2, the top surface (e.g., epidermis) of the target 106 has irregularities as do the subsurface layers 220. While the top surface of the target 106 generates a substantially specular reflection 204 of the polarized light signal 105, the subsurface layers 220 in turn generate first, second, and third substantially diffused reflections 206, 208, and 210 from layers $t_1$, $t_2$, and $t_3$. Referring back to FIG. 1, the specular and diffused reflections can be directed to a second polarizer 110 of device 100.

The second polarizer 110 can also use different polarization techniques as described above. However, for the present illustration, the second polarizer 110 is also assumed to be a linear polarizer. When the first and second polarizers 104, 110 differ in their polarization states, a mixed polarization state occurs, which changes the polarization of the specular and diffused reflections 204-210. For example, when the polarization states of the first and second polarizers 104, 110 are orthogonal to each other, the mixed polarization state resulting from this combination substantially filters (eliminates) the specular reflection 204. As the polarization states of the first and second polarizers 104, 110 are gradually adapted to be less than orthogonal to each other, one or more of the diffused reflections 206-210 begin to be filtered in whole or in part, while the specular reflection 204 begins to pass through the second polarizer 110. As the polarization states of the first and second polarizers 104, 110 continue to be modified in relation to each other, different diffused reflections are filtered. Thus, varying the filtering of diffused reflections according to changes applied to the mixed polarization state serves as one modality for modifying an observable range of subsurfaces of the target 106. Changes to the mixed polarization state can also be used to enhance the contrast of a subsurface feature of the target 106. The tunable light sources 102 can serve as a second modality for modifying spectral images of observable features of the target 106.

Figure 3:
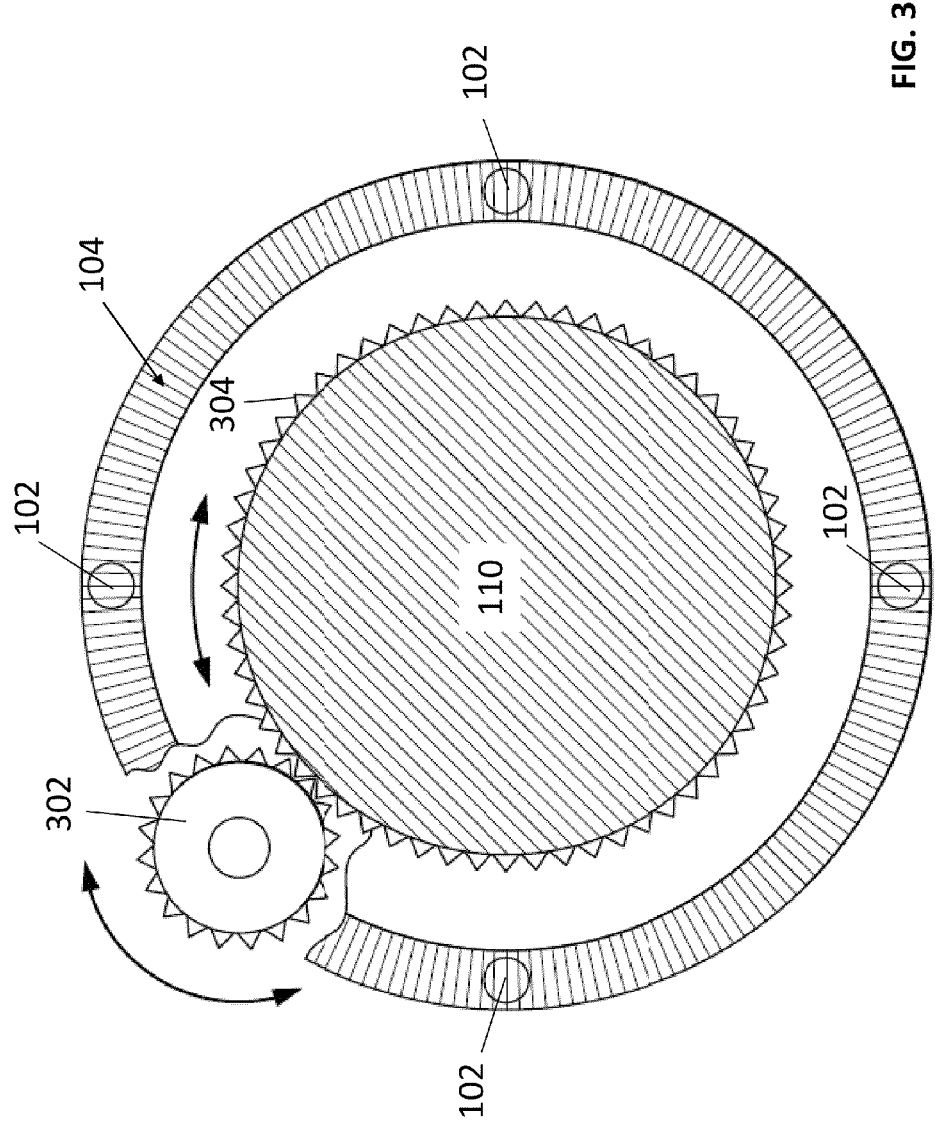
FIGS. 3-4 depict illustrative embodiments of a mechanism for adjusting a mixed polarization state of the device of FIG. 1 to modify an observable range of subsurfaces of the target.
Figure 4:
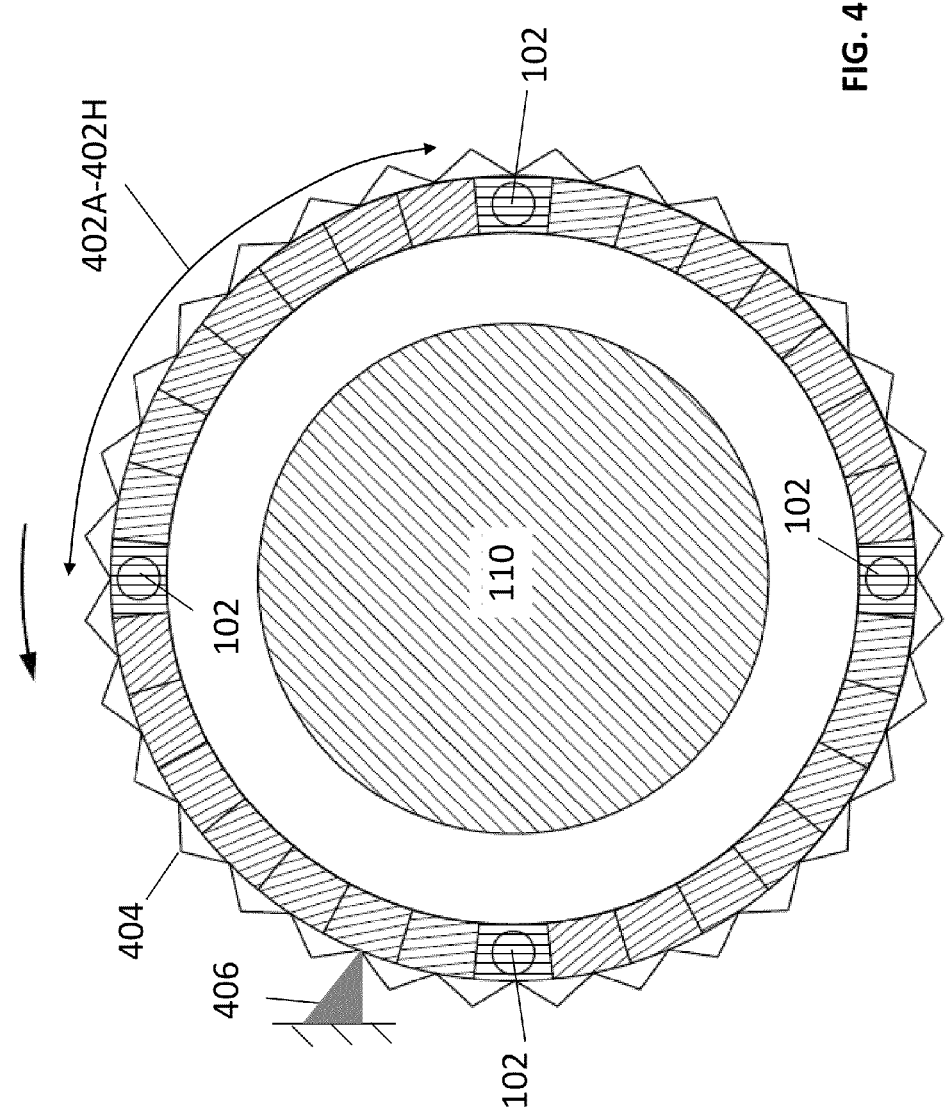

FIGS. 3-4 depict illustrative embodiments of a mechanism for adjusting the mixed polarization state to modify an observable range of subsurfaces of the target 106. In a first embodiment shown in FIG. 3, the device 100 can have four light sources 102 such as, for example, four tunable LEDs. The light sources 102 can be incident with the first polarizer 104, which is constructed as a ring having a linear polarization shown by the "hash" lines. The first polarizer 104 can be fixed in position in this illustration. The second polarizer 110, however, can be adapted to rotate with a gear 302 coupled to cogs 304 of the second polarizer 110. As the gear 302 is turned the polarization state of the second polarizer 110 changes relative to the polarization state of the first polarizer 104, thereby adjusting the mixed polarization state. Changes in the mixed polarization state causes a change in filtering of the diffused reflections when the polarization lines of the first and second polarizers are less than orthogonal to each other.

In another embodiment, the first polarizer 104 can be configured with polarization windows 402A through 402H, each polarization window having a different polarization state as shown in FIG. 4. As the first polarizer 104 is rotated counterclockwise a window at a time by way of cogs 404, a new polarization state is applied to the four light sources 102 simultaneously. An alignment cog 406 can be used to center the windows 402 for rotational increment. The polarization windows 402A-H can be chosen so that each time the first polarizer 104 is rotated to a new window, each of the four light sources 102 encounters the same polarization state.

Referring back to FIG. 1, the device 100 can further comprise an optical device in the form of doublet lens 112, which can be used to focus the specular and diffused reflections 204-210 generated by the target 106. The reflections can be directed to an image sensor 114 such as a charge-coupled device (CCD) sensor which can generate images from the specular and diffused reflections sensed from the target 106. The images generated by the image sensor 114 can be directed to a display as will be described below.

Figure 5:
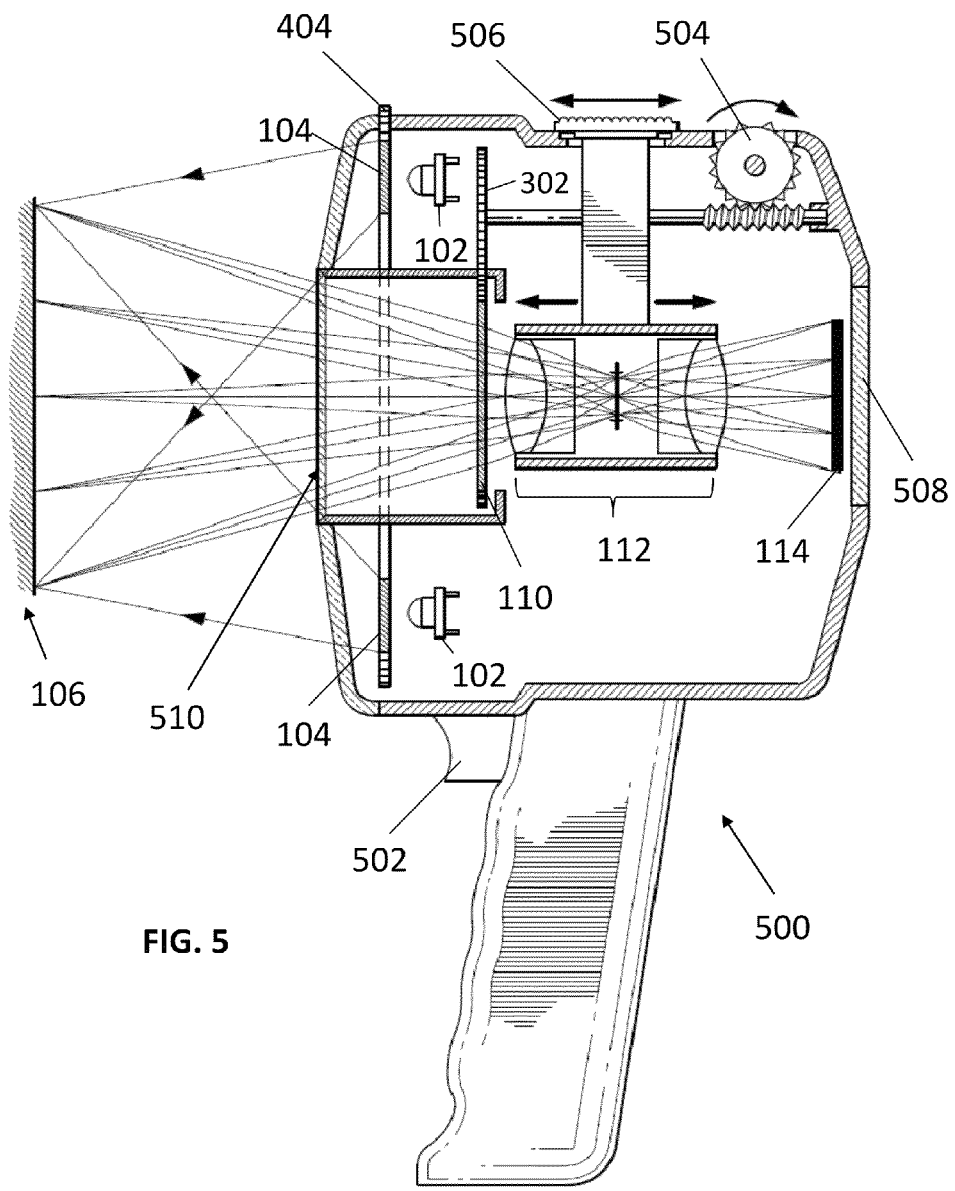
FIG. 5 depicts an illustrative embodiment of a housing assembly of the device of FIGS. 1 and 3-4.

FIG. 5 depicts an illustrative embodiment of a housing assembly 500 that can be used for carrying components of the device 100 of FIGS. 1 and 3-4. In this illustration, the light sources 102 can be assembled in a fixed portion of the housing assembly 500. The first polarizer 104 can be assembled in the housing assembly 500 so that it is incident to light signals from the light sources 102. To accommodate the embodiment of FIG. 4, the first polarizer 104 can be assembled in the housing assembly 500 so that the cogs 404 are at least partially exposed and accessible for manual rotation of the first polarizer 104. The cogs 404 can be designed to intersect with alignment cog 406 (not shown in FIG. 5) so that the each polarized window is centered on the light source 102 for each rotation between windows 402A through 402H. In another embodiment, a first mechanism 504 can be coaxially coupled to the second polarizer 110 by way of the gear 302 to rotate the second polarizer 110 as described in FIG. 3. The rotation of the first polarizer 104, second polarizer 110, or both can change the mixed polarization state of the polarizers, and thereby modify an observable range of diffused reflections from the target 106.

A second mechanism 506 can be added to the housing assembly 500 to enable movement of the optical device 112. The second mechanism 506 can be configured to change the focal point of light signals generated by the doublet lenses as well as enabling a user to zoom in or out of images generated by the image sensor 114. The second mechanism 506 can be adapted to change the positions of each lens in the doublet 112 relative to each other and the image sensor 114 to adjust the focal point or zoom the image of the device 100. The image sensor 114 can be adapted to present images at a display 508 attached to the housing assembly 500. The housing assembly 500 can also include a trigger 502, which when pressed can be used to initiate a process such as, for example, the emission of light signals from the light sources 102.

Figure 6:
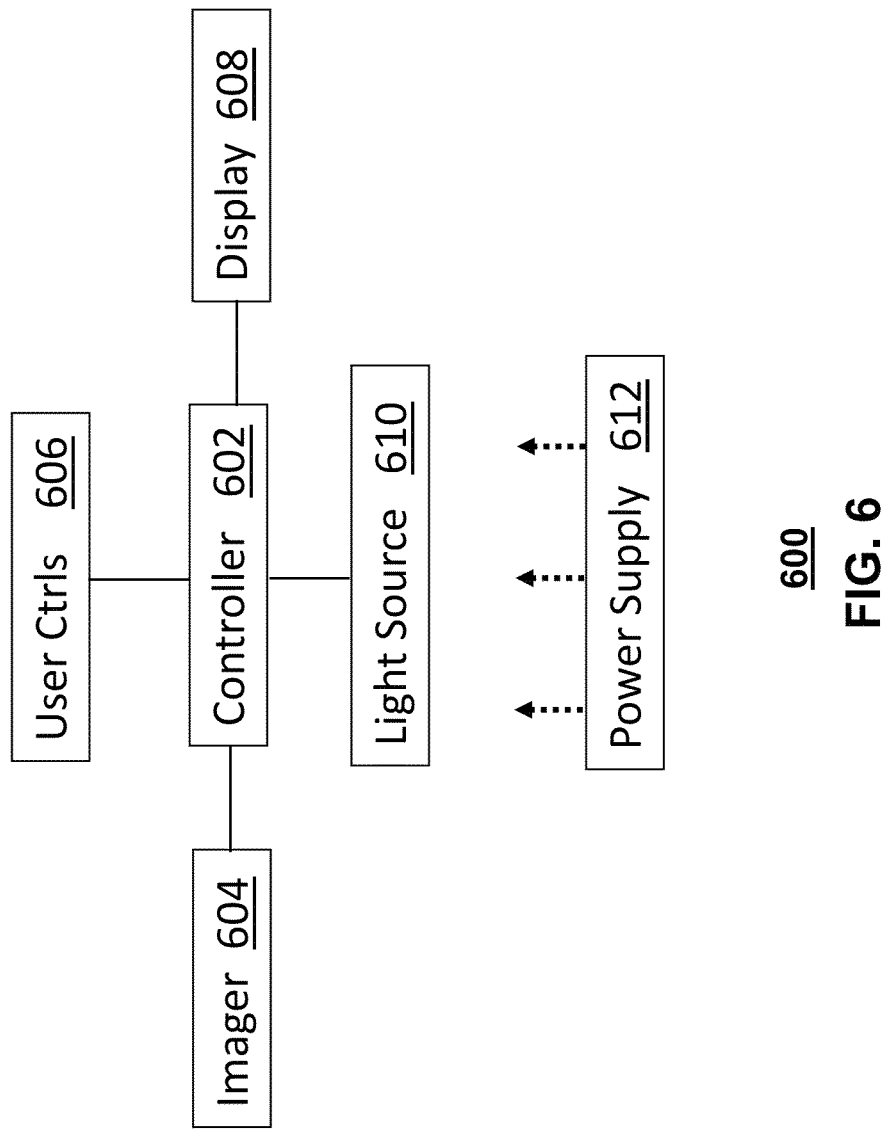
FIG. 6 depicts a system diagram of electronic components of the device of FIG. 1.

FIG. 6 depicts a system 600 illustrating embodiments of electronic components utilized by the device 100 of FIGS. 1 and 5. In this embodiment, the device 100 comprises a controller 602, an imager 604, user controls 606, a display 608, a light source 610, and a power supply 612. The imager 604 can comprise the optical device 112 and image sensor 114 shown in FIGS. 1 and 5. In one embodiment, for example, the optical device 112 can be calibrated during the manufacture of the device 100 to permanently set the focal point. In this embodiment, the mechanical control 506 can be eliminated.

In another embodiment, the imager 604 can be supplemented with auto-focusing technology. In this embodiment, the mechanical controls 506 can be replaced in whole or in part with electro-mechanical components that include gears and/or shafts manipulated by linear or stepper motors with an auto-focus sensor to control movement of the optical device 112. Auto-focusing techniques such as passive auto focusing can be used to determine the location of the target 106. For example, phase detection can be used by dividing incoming light into pairs of images and comparing them. The phase difference between the images can be measured using image processing means to determine where to adjust a focal point of light signals generated by the optical device 112.

The phase difference calculated by the controller 602 can be used to direct an adjustment of the lens doublet 112 by way control signals sent to the linear or step motors to adjust the focal point of the mixed polarized light signals generated by the lens doublet 112. The electro-mechanical device can also be adapted to provide a zooming in and zooming out feature by controlling the distance between the lens doublets 112 and by moving one or both lens towards or away from the image sensor 114 shown in FIG. 5. In yet another embodiment, the user controls 606 can be mechanical controls 506 which are manipulated by user input such as shown in FIG. 5. In this embodiment, the mechanical controls 506 can be designed to manually control focusing and/or zooming without assistance of the controller 602.

The user controls 606 can also include the trigger 502 for enabling lighting as an "on"/"off" switch. The housing assembly 500 of FIG. 5 can also include controls (not shown) for presetting a desired range of wavelengths for light signals generated by the light source 102. In one embodiment, a thumbwheel can be added to the housing assembly 500, which when turned, can cause the controller 602 to direct the tunable light sources 102 to change the wavelength of light signals emitted from the light sources in unison. In another embodiment, the trigger 502 can be used in place of the thumbwheel to adjust lighting. As the trigger 502 is gradually pushed in or released partially, the light signals generated by the light sources 102 can be changed under direction of the controller 602. In another embodiment, multiple thumbwheels can be added to the housing assembly 500 when it is desirable to control the wavelength of light signals generated by each light source 102 independently. In yet another embodiment, the light sources 102 can be controlled from the display 508 via a graphical user interface (GUI). In this embodiment, mechanical control buttons can be added to the display section (view not shown in FIG. 5), or the display 508 can be a touch-screen display with selectable controls in the GUI.

In one embodiment, the user controls 606 can further include mechanical controls 404 and/or 504 shown in FIG. 5 for controlling the mixed polarization state of the first and second polarizers 104, 110. In this embodiment, the controls 404, 504 can be manual gear-driven controls such as shown in FIGS. 3-5. In another embodiment, mechanical controls 404 and 504 can be replaced in whole or in part with electro-mechanical components that include gears and/or shafts manipulated by linear or stepper motors for rotating the first polarizer 104, the second polarizer 110, or both under the control of the controller 602. A user of the device 100 can request a change of the mixed polarization state by way of manual buttons or touch-screen GUI controls presented by the display 508 as described above.

The display 608 can be a display 508 attached to the device 100 such as shown in FIG. 5, and/or a computer display coupled to the device 100 by way of a tethered interface (e.g., VGA, or DVI port of the device—not shown in FIG. 5) or by wireless means. If by wireless means, system 600 can further include a wireless transmitter for transmitting data to a local system. The display 508 can be a monochrome or color LCD (Liquid Crystal Display), OLED (Organic Light Emitting Diode) or other suitable display technology for conveying images to an end user. As noted above the display 508 can be a touch-screen display, or a display with a keypad and navigation buttons (e.g., up, down, right and left buttons, or navigation disk).

The controller 602 can utilize computing technologies such as a microprocessor, a digital signal processor (DSP), and/or a video processor with associated storage memory such as Flash, ROM, RAM, SRAM, DRAM or other storage technologies for detecting, processing and controlling the imager 604, the polarizers 104, 110, the display 608, the light source 610, and the power supply 612.

The power supply 612 can utilize power management technologies such as replaceable and rechargeable batteries, supply regulation technologies, and charging system technologies for supplying energy to the components of the device 100 to facilitate portable applications. Alternatively, the power supply 612 can represent an external power source such as DC power supplied over a tethered interface such as a cable coupled to a DC power supply.

Figure 7:
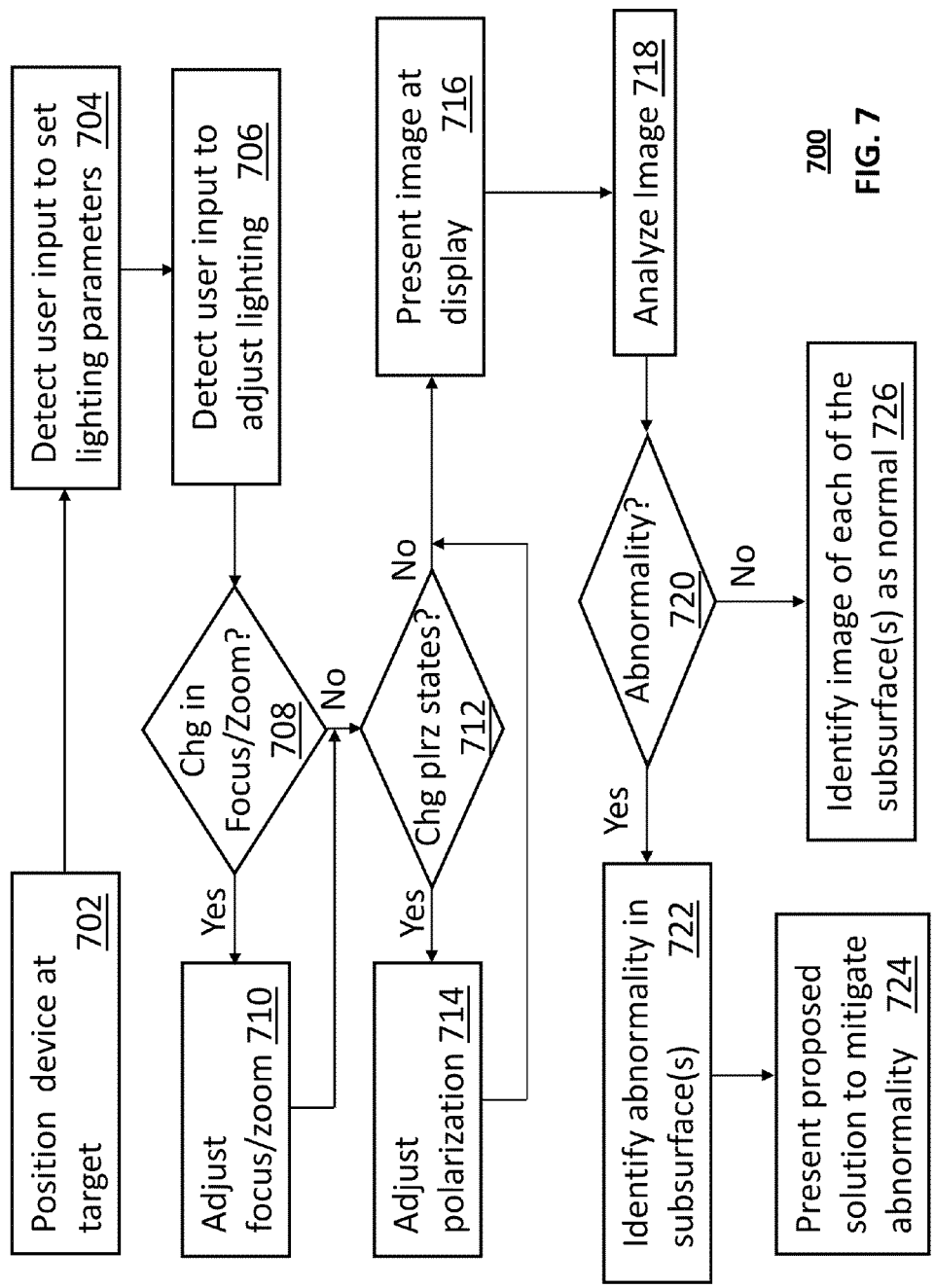
FIG. 7 depicts an illustrative embodiment of a method operating in portions of the device shown in FIGS. 1, 3-6.

FIG. 7 depicts an illustrative embodiment of a method 700 operating in portions of the device 100 shown in FIGS. 1, 3-6. Method 700 can begin with step 702 where the device 100 is positioned at the target 106. This step can represent placing a front portion 510 of the housing assembly 500 centered about the target 106. At step 704, the controller 602 can be operable to detect user input for presetting lighting parameters such as a desired range of wavelengths of the light source(s) 102, light intensity, and so on by means described earlier (e.g., user input at touch-screen display 508) as a first modality for analyzing features of the target 106. At step 706, the controller 602 can be operable to detect user input to enable the light source(s) 102 to emit light according to the parameters set in step 704. This can be accomplished by the controller 602 detecting a depression of the trigger 502. At step 708, the controller 602 can detect a request for adjusting focus of the mixed polarization light signals, which it performs in step 710. The request for a focus adjustment can originate from user input at the user controls 606, or from auto-focusing technology discussed above. In step 708, the controller 602 can also monitor the user controls 606 for a zoom adjustment request, which it performs in step 710 in a manner described earlier.

Step 712 can represent a request to change the mixed polarization state as a second modality for analyzing the target 106, which is performed in step 714 based on the embodiments described earlier. The request can originate from user controls 606 such as by way of manual adjusts described in FIGS. 3-5. Alternatively, a change in the mixed polarization state can be implemented by the controller 602, which detects a request for a change in the mixed polarization state from user controls 606 and in response signals linear or stepper motors to adjust gears and/or shafts to modify the polarization state of the first polarizer 104, the second polarizer, or both.

The combination of adjusting the wavelengths of light generated by the tunable light sources 102 and adjusting the mixed polarization state provides for two modalities to analyze features of the target 106. The modality of adjusting wavelengths of light provides a modality for enhancing different features of the target 106 such as, for example, in human tissue enhancing the observability of blood vessels, fat, collagen fibers, and so on. The modality of adjusting the mixed polarization provides for sensing diffused reflections of the polarized signal 105 at varying depths of the target 106, and provides the ability to change aspects of the diffused reflections of the polarized light signal 105 such as contrast, light intensity, resolution, and so on.

At step 716 the controller 602 can utilize image processing techniques to present a GUI at the display 508 (or local computer display) to present the observable range of subsurfaces of the target 106 according to the mixed polarized light signals sensed by the image sensor 114 of FIGS. 1 and 5. At step 718, the controller 602 can be further operable to automatically analyze the target 106 using image and signal processing techniques. This step can be accomplished by statistical modeling of normal versus abnormal targets, or by recording signal profiles and/or image profiles of normal and abnormal targets, which can be retrieved from a database stored in the device 100 or at a remote database (not shown) accessible by the device 100 over a network interface (e.g., the Internet) or other suitable means. Image and signal processing software can be utilized by the device 100 to determine in step 720 from a signal profile of the mixed polarization light signals a presence and type of abnormality by comparing the detected light signals to normal and abnormal profiles retrieved from the local or remote database. Such profiles can be collected in clinical trials using statistical modeling and/or other techniques suitable for profiling targets.

If no abnormalities are detected, the controller 602 proceeds to step 726 where it presents the image and/or plots of the subsurfaces of the target 106 according to the mixed polarization light signals detected by the image sensor 114. If an abnormality in the target 106 is detected by the controller 602, the controller 602 can proceed to step 722 where it can identify the abnormality in the image or plot of the subsurfaces of the target 106 with indicator(s) such as arrows pointing to the abnormal feature(s) with text descriptors. The controller 602 can be further adapted in step 724 to analyze the abnormality and propose a solution to mitigate the abnormality. In a medical setting, the proposed solution could be, for example, a proposed prescription of medicine or method of treatment for a patient. The proposed solution can be retrieved by the device 100 from a local or remote database providing mitigating techniques according to the detected abnormality. In an industrial setting, the proposed solution could be an identification of an area of the target 106 with defects (e.g., fractures) that should be avoided.

Upon reviewing the aforementioned embodiments, it would be evident to an artisan with ordinary skill in the art that said embodiments can be modified, reduced, or enhanced without departing from the scope and spirit of the claims described below. For example, user input can be provided by a user of the device 100 by way of a GUI presented by the display 508 to identify a type of target being analyzed by the user. A clinician can enter via the GUI of the display 508 that skin tissue is being analyzed for melanoma. The target description given by the user can be used by the controller 602 of the device 100 to retrieve from a local or remote database configurations and/or profiles for analyzing the identified target type.

A retrieved configuration can be used by the controller 602 to automatically configure the light sources 102 (color schemes, light intensity, etc.), and the first and second polarizers 102, 104 for initiating a desired sequence of mixed polarization states. The controller 602 can also be configured according to the user identified target type to retrieve from the database signal profiles for identifying a normal target versus an abnormal target, and for proposing mitigation techniques when an abnormality is detected. The controller 602 can further be configured according to the user identified target type to utilize specific image processing algorithms for analyzing and presenting at the display 508 images associated with the mixed polarized light signals sensed by the image sensor 114.

System 600 can be adapted in some applications to automatically adjust the wavelengths of light generated by the tunable light sources 102 and to adjust the mixed polarization state simultaneously. In this embodiment, the controller 602, for example, can be adapted to perform a sweep of wavelengths of light while at the same time performing a sweep of mixed polarization states. The combined sweeps result in a variety of diffused reflections of varying wavelengths and signal intensity, which can be sensed by the image sensor 114, recorded in memory, and analyzed by a spectrometer (not shown in FIG. 6). The spectrometer can provide a user of the device 100 spectral signal plots, as well as two or three dimensional images of subsurfaces of the target 106, which can be directed to the device 100 via a tethered or wireless interface for presentation by way of the display 508. Alternatively, the spectrometer can present the results of the analysis at a local computer monitor.

Other suitable modifications of the foregoing embodiments are contemplated by the subject disclosure.

Figure 8:
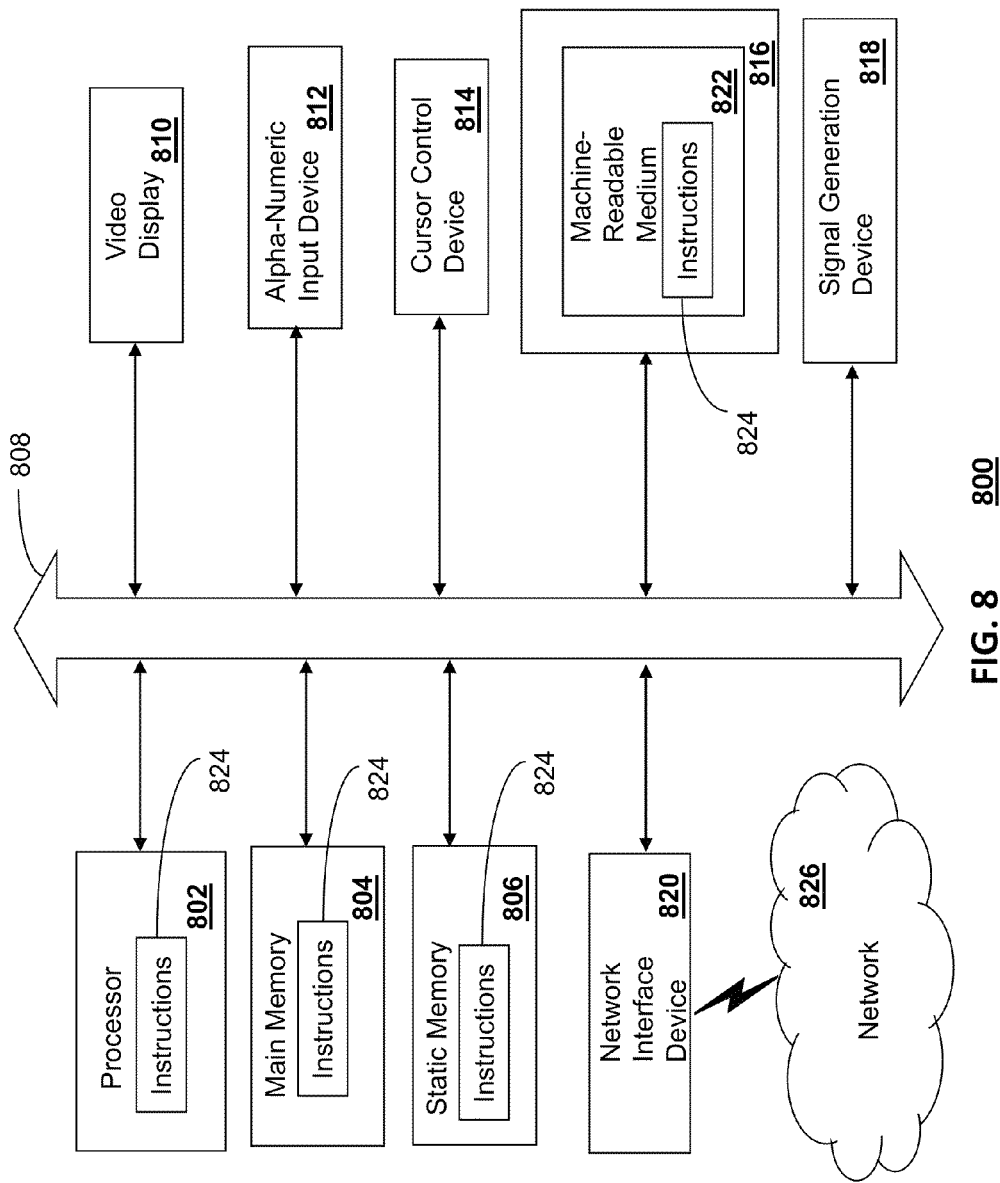
FIG. 8 is a diagrammatic representation of a machine in the form of a computer system within which a set of instructions, when executed, may cause the machine to perform any one or more of the methods described herein.

FIG. 8 depicts an exemplary diagrammatic representation of a machine in the form of a computer system 800 within which a set of instructions, when executed, may cause the machine to perform any one or more of the methods discussed above. One or more instances of the machine can operate, for example, as the components shown in FIGS. 5-6. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 800 may include a processor 802 (e.g., a central processing unit (CPU), a graphics processing unit (GPU, or both), a main memory 804 and a static memory 806, which communicate with each other via a bus 808. The computer system 800 may further include a video display unit 810 (e.g., a liquid crystal display (LCD), a flat panel, or a solid state display. The computer system 800 may include an input device 812 (e.g., a keyboard), a cursor control device 814 (e.g., a mouse), a disk drive unit 816, a signal generation device 818 (e.g., a speaker or remote control) and a network interface device 820.

The disk drive unit 816 may include a tangible computer-readable storage medium 822 on which is stored one or more sets of instructions (e.g., software 824) embodying any one or more of the methods or functions described herein, including those methods illustrated above. The instructions 824 may also reside, completely or at least partially, within the main memory 804, the static memory 806, and/or within the processor 802 during execution thereof by the computer system 800. The main memory 804 and the processor 802 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 822 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA, LTE) are contemplated for use by computer system 800.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, are contemplated by the subject disclosure.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:
1. A device, comprising:
a light source that facilitates emitting a light signal operating in a region of a light spectrum;
a first polarizer comprising a first portion, wherein the first portion is incident with the light signal, and wherein the first portion has a first polarization state that facilitates polarizing the light signal to generate a polarized light signal directed to a target tissue;

a second polarizer comprising a second portion, wherein the second portion is incident with a substantially specular reflection of the polarized light signal emitted from a top surface of the target tissue and incident with a substantially diffused reflection of the polarized light signal emitted from subsurfaces of the target tissue, wherein the second portion has a second polarization state, and wherein a combination of the first polarization state and the second polarization state creates a mixed polarization state for generating mixed polarized light signals from the substantially specular reflection and the substantially diffused reflection of the polarized light signal;

a mechanical control that facilitates adjusting the mixed polarization state to generate adjusted mixed polarized light signals that modify an observable range of the subsurfaces of the target tissue;

an imager that facilitates presenting the modified observable range of the subsurfaces of the target tissue according to the adjusted mixed polarized light signals; and a controller that facilitates:

receiving user-generated input identifying a type of target to be analyzed;

retrieving configuration information for adjusting the mixed polarization state according to the type of target;

controlling the mechanical control to adjust the mixed polarization state according to the configuration information by performing a first sweep of wavelengths of light from the light source and a second sweep of mixed polarization states;

generating an image from the adjusted mixed polarized light signals;

detecting an abnormal feature in the image, and presenting the image with an indicator indicating a location of the abnormal feature in the image.

2. The device of claim 1, wherein the mechanical control adjusts the mixed polarization state by adjusting one of the first polarization state of the first portion or the second polarization state of the second portion.

3. The device of claim 1, wherein the light source comprises one of one or more tunable light emitting diodes, or one or more fibers coupled to one or more tunable light sources.

4. The device of claim 1, wherein at least one of the first polarizer, the second polarizer, or both is configured as a linear polarizer, a circular polarizer, an elliptical polarizer, or combinations thereof.

5. The device of claim 1, wherein the controller controls the light source to selectively configure the light signal to emit a desired range of wavelengths of light.

6. The device of claim 1, wherein the mechanical control is a motor coupled to at least one of the first polarizer, the second polarizer, or both, and wherein the controller causes the motor to adjust at least one of the first polarization state of the first polarizer, the second polarization state of the second polarizer, or both.

7. The device of claim 1, wherein the mechanical control is a rotatable mechanism coupled to at least one of the first polarizer, the second polarizer, or both, and wherein rotatable mechanism is operable to adjust at least one of the first polarization state of the first polarizer, the second polarization state of the second polarizer, or both, wherein the detecting of the abnormal feature in the image comprises comparing the adjusted mixed polarized light signals to a profile of a normal target, and wherein the controller further presents in the image a descriptor descriptive of the abnormal feature.

8. The device of claim 1, wherein the light source comprises one or more tunable light sources.

9. The device of claim 1, wherein the imager comprises an optical device and an image sensor.

10. The device of claim 8, wherein each of the one or more tunable light sources is tunable to a desired range of wavelengths of light.

11. The device of claim 8, wherein the first portion comprises one or more polarized portions polarized according to the first polarization state, wherein light signals generated by the one or more tunable light sources are incident with the one or more polarized portions.

12. The device of claim 9, wherein the image sensor comprises a charge-coupled device sensor.

13. The device of claim 9, wherein the optical device comprises a plurality of optical devices.

14. The device of claim 13, comprising a second mechanical control for controlling at least one of a zoom in feature of the plurality of optical devices, a zoom out feature of the plurality of optical devices, a focusing feature of the plurality of optical devices, or combinations thereof.

15. A method, comprising:

generating from a light source a light signal operating in a region of a light spectrum;

modifying the light signal with a first polarizer having a first polarization state to generate a polarized light signal directed to a target;

modifying a substantially specular reflection and a substantially diffused reflection of the polarized light signal generated from the target with a second polarizer having a second polarization state to generate mixed polarized light signals having a mixed polarization state;

receiving user-generated input identifying a type of target to be analyzed;

retrieving configuration information according to the type of target;

adjusting the mixed polarization state according to the configuration information by performing a first sweep of wavelengths of light from the light source and a second sweep of mixed polarization states, wherein the adjusting generates adjusted mixed polarized light signals that modify an observable range of subsurfaces of the target;

generating an image from the adjusted mixed polarized light signals;

detecting an abnormal feature in the image; and presenting the image with an indicator indicating a location of the abnormal feature in the image.

16. The method of claim 15, wherein the detecting of the abnormal feature in the image comprises comparing the adjusted mixed polarized light signals to a profile of a normal target.

17. The method of claim 15, wherein the adjusting of the mixed polarization state comprises adjusting at least one of the first polarization state, the second polarization state, or both.

18. The method of claim 15, further comprising presenting in the image a text descriptor descriptive of the abnormal feature.

19. The method of claim 15, further comprising adjusting the light signal of the light source to enhance the observable range of the subsurfaces of the target.

20. The method of claim 15, wherein the target comprises a biological material.

21. The method of claim 15, wherein the target comprises a non-biological material.

22. A method, comprising:
- assembling in a device a first polarizer and a light source that facilitates polarizing a light signal emittable by the light source according to a first polarization state of the first polarizer to generate a polarized light signal;
- assembling in the device a second polarizer that facilitates modifying a substantially specular reflection and a substantially diffused reflection of the polarized light signal generated by a target according to a second polarization state of the second polarizer;
- assembling in the device a mechanical control that facilitates adjusting at least one of the first polarization state, the second polarization state, or both to generate adjusted mixed polarized light signals having a mixed polarization state that modify an observable range of subsurfaces of the target; and
- assembling in the device a controller that facilitates:
  - receiving input identifying a type of target to be analyzed;
  - retrieving configuration information for adjusting the mixed polarization state according to the type of target;
  - controlling the mechanical control to adjust the mixed polarization state according to the configuration information by performing a first sweep of wavelengths of light from the light source and a second sweep of mixed polarization states;
  - generating an image of the observable range of subsurfaces of the target from the adjusted mixed polarized light signals, detecting an abnormal feature in the image; and
  - presenting the image with an indicator indicating a location of the abnormal feature in the image.

23. The method of claim 22, comprising assembling in the device an optical device for performing at least one of focusing the observable range of subsurfaces of the target, zooming into the observable range of subsurfaces of the target, zooming out of the observable range of subsurfaces of the target, or any combination thereof.

24. The method of claim 22, comprising assembling in the device an image sensing device for sensing the image of the observable range of subsurfaces of the target.

25. The method of claim 24, comprising assembling in the device a display for presenting the image of the observable range of subsurfaces of the target.

26. A non-transitory computer-readable storage medium, comprising computer instructions, which when executed by a processor, cause the processor to perform operations comprising:
- enabling a light source to emit a light signal at a desired range of wavelengths of light, wherein the light signal is polarized by a first polarizer having a first polarization state to generate a polarized light signal directed to a target, and wherein a substantially specular reflection and a substantially diffused reflection of the polarized light signal generated from the target is modified with a second polarizer having a second polarization state to generate mixed polarized light signals having a mixed polarization state;
- receiving input identifying a type of target to be analyzed;
- retrieving configuration information according to the type of target;
- controlling a mechanical control according to the configuration information by performing a first sweep of wavelengths of light from the light source and a second sweep of mixed polarization states to adjust at least one of the first polarization state, the second polarization state, or both to generate adjusted mixed polarized light signals that modify an observable range of subsurfaces of the target;
- generating an image from the adjusted mixed polarized light signals;
- detecting an abnormal feature in the image; and
- presenting the image with an indicator indicating a location of the abnormal feature in the image.

27. The non-transitory computer-readable storage medium of claim 26, wherein the detecting of the abnormal feature in the image comprises comparing the adjusted mixed polarized light signals to a profile of a normal target.

28. The non-transitory computer-readable storage medium of claim 26, wherein the operations further comprise controlling the light source to modify the desired range of wavelengths of light in the light signal to enhance one or more features of the observable range of subsurfaces of the target.

29. The non-transitory computer-readable storage medium of claim 26, wherein the generating of the image comprises sensing the image with an image sensor that detects the mixed polarized light signals.

30. The non-transitory computer-readable storage medium of claim 29, wherein the operations further comprise presenting in the image a descriptor descriptive of the abnormal feature.

* * * * *